United States Patent
Barrus

(10) Patent No.: US 10,952,778 B2
(45) Date of Patent: Mar. 23, 2021

(54) ROD REDUCER

(71) Applicant: K2M, Inc., Leesburg, VA (US)

(72) Inventor: Michael Barrus, Redondo Beach, CA (US)

(73) Assignee: K2M, Inc., Leesburg, VA (US)

( * ) Notice: Subject to any disclaimer, the term of this patent is extended or adjusted under 35 U.S.C. 154(b) by 43 days.

(21) Appl. No.: 16/342,435

(22) PCT Filed: Oct. 18, 2017

(86) PCT No.: PCT/US2017/057188
§ 371 (c)(1),
(2) Date: Apr. 16, 2019

(87) PCT Pub. No.: WO2018/075639
PCT Pub. Date: Apr. 26, 2018

(65) Prior Publication Data
US 2019/0247101 A1     Aug. 15, 2019

Related U.S. Application Data

(60) Provisional application No. 62/409,607, filed on Oct. 18, 2016.

(51) Int. Cl.
*A61B 17/70* (2006.01)
*A61B 17/00* (2006.01)

(52) U.S. Cl.
CPC ...... *A61B 17/7086* (2013.01); *A61B 17/7032* (2013.01); *A61B 2017/00367* (2013.01); *A61B 2017/00477* (2013.01)

(58) Field of Classification Search
CPC ............ A61B 17/7088; A61B 17/7089; A61B 17/7086
See application file for complete search history.

(56) References Cited

U.S. PATENT DOCUMENTS

| 8,308,774 B2 | 11/2012 | Hoffman et al. |
| 9,452,000 B2 | 9/2016 | Barrus |
| (Continued) | | |

OTHER PUBLICATIONS

Extended European Search Report for EP17861302.2 dated Jun. 5, 2020; 3 pages.

(Continued)

*Primary Examiner* — Jan Christopher L Merene
(74) *Attorney, Agent, or Firm* — Lerner, David, Littenberg, Krumholz & Mentlik, LLP

(57) ABSTRACT

A rod reducer includes a shaft, a sleeve assembly defining a bore dimensioned to receive the shaft therethrough, a housing defining a bore dimensioned to receive the shaft, arm members operatively associated with the housing, and an anvil operatively coupled with the shaft. The sleeve assembly includes a locking tab. The housing includes a groove configured to selectively receive the locking tab of the sleeve assembly. The housing includes a locking ledge portion in registration with the groove. The anvil is transitionable between a proximal position, in which, the arm members are spaced apart, and a distal position, in which, the arm members are in an approximated position. The sleeve assembly is rotatable between an engaged state in which, the locking ledge portion inhibits relative axial displacement of the sleeve assembly with the housing, and a disengaged state in which, the sleeve assembly is axially movable relative to the housing.

20 Claims, 9 Drawing Sheets

(56) References Cited

U.S. PATENT DOCUMENTS

| | | | |
|---|---|---|---|
| 2009/0018593 A1* | 1/2009 | Barrus | A61B 17/8875 |
| | | | 606/86 A |
| 2012/0191144 A1* | 7/2012 | Peultier | A61B 17/7086 |
| | | | 606/86 A |
| 2015/0066042 A1 | 3/2015 | Cummins et al. | |
| 2015/0100097 A1* | 4/2015 | Barrus | A61B 17/7085 |
| | | | 606/86 A |
| 2015/0100098 A1 | 4/2015 | Moore | |
| 2016/0206354 A1 | 7/2016 | Mladenov et al. | |
| 2016/0346011 A1* | 12/2016 | Angus | A61B 17/7032 |
| 2018/0140337 A1* | 5/2018 | Noordeen | A61B 17/70 |

OTHER PUBLICATIONS

International Search Report for PCT/US2017/057188 dated Dec. 28, 2017.

* cited by examiner

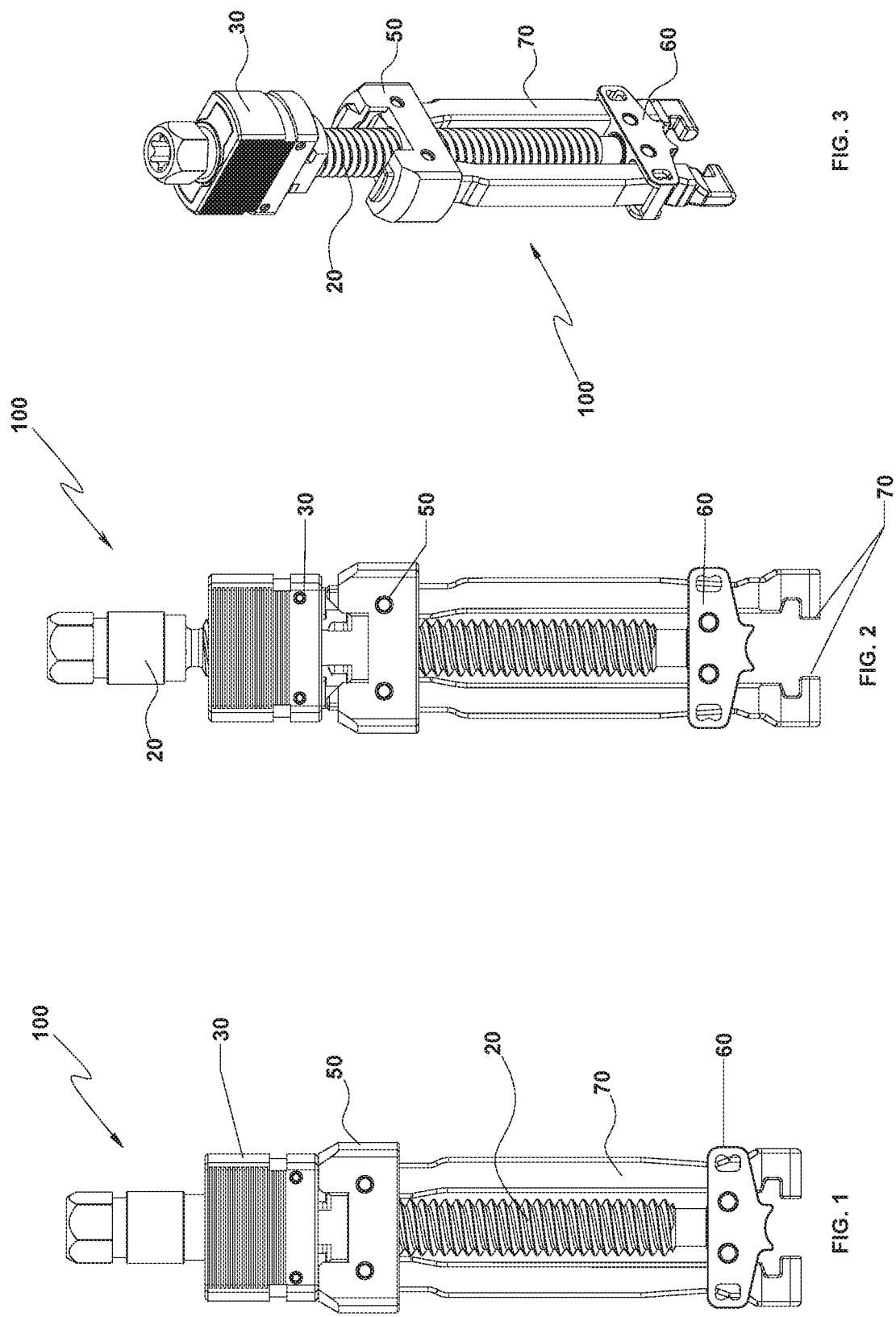

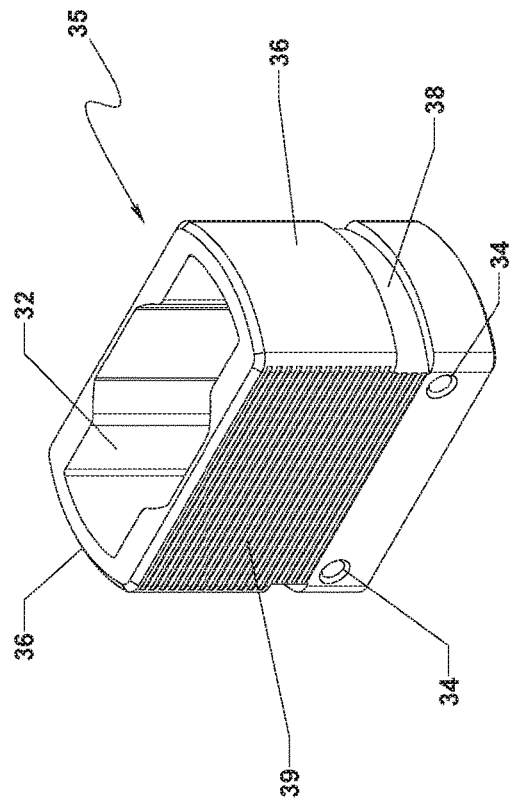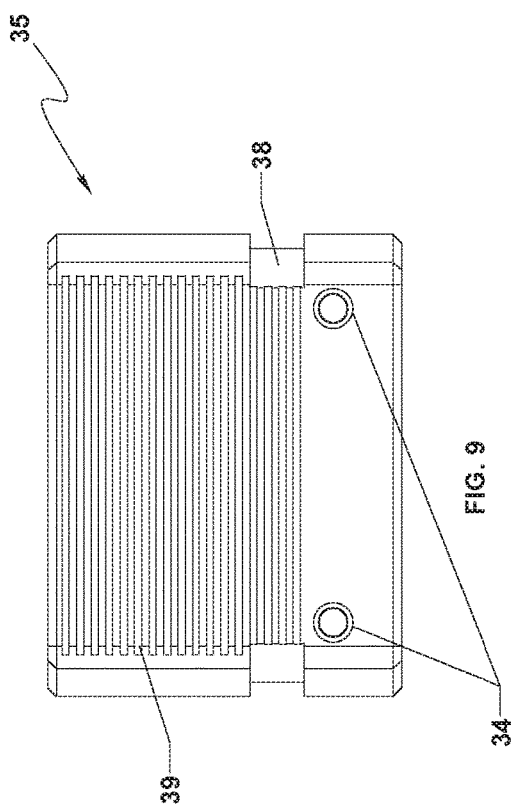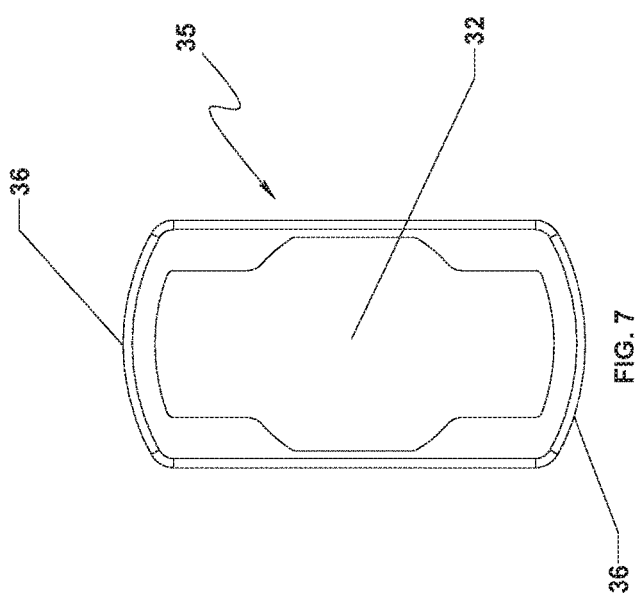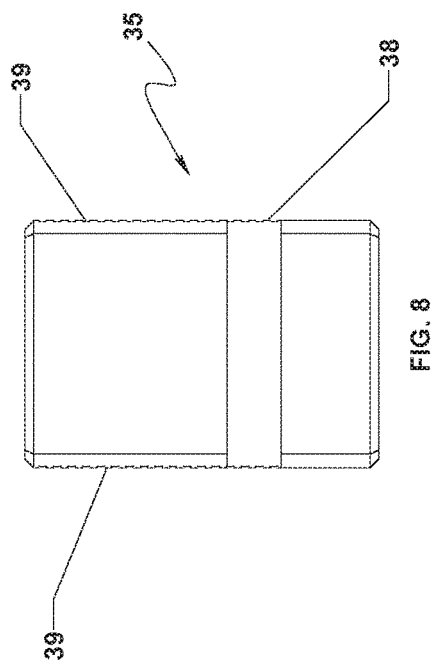

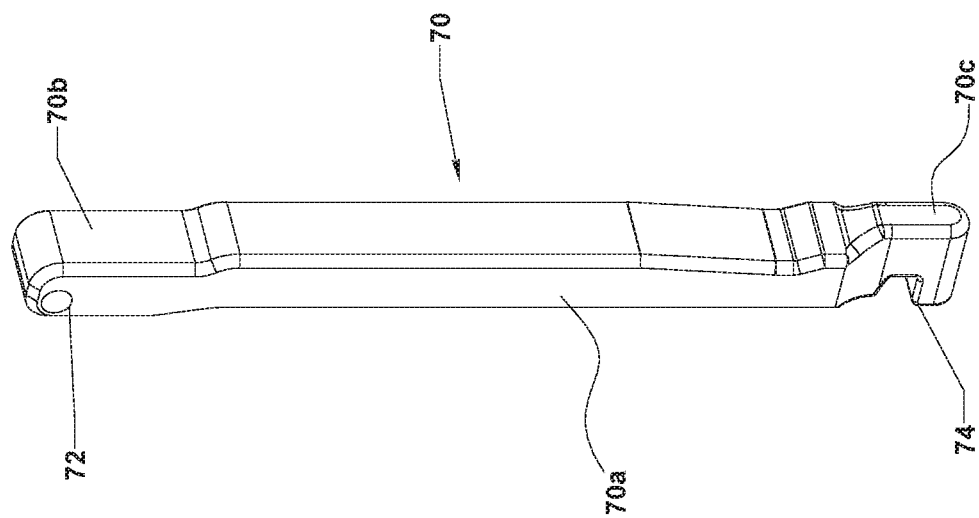

ROD REDUCER

CROSS-REFERENCE TO RELATED APPLICATION

The present application is a national phase entry under 35 U.S.C. § 371 of International Application No. PCT/US2017/057188, filed Oct. 17, 2017, which claims the benefit of U.S. Provisional Application Ser. No. 62/409,607, which was filed on Oct. 18, 2016, the entire contents of which is incorporated herein by reference.

BACKGROUND

Technical Field

The present disclosure relates to a spinal deformity correction device and, more particularly, to a manually operated rod reducer for reducing a spinal rod into a bone screw in a controlled and measured manner.

Description of Related Art

The spine is made up of a superposition of vertebrae that are normally aligned along a vertebral axis, extending from the lumbar vertebrae to the cervical vertebrae. There are many known spinal conditions, e.g., scoliosis, that require the imposition and/or maintenance of corrective forces on the spine in order to return the spine to its normal condition. When an individual's spine presents abnormal curvature, the vertebrae are inclined relative to one another and relative to the vertebral axis. The lateral edges of the vertebrae situated on one side are thus closer to one another and form a concave curve, while the lateral edges on the other side appear spaced apart from one another and form a convex curve. In order to straighten the spinal column, the lateral edges of the vertebrae on the concave side are spaced apart from one another and are taken relative to one another to a distance that is substantially equivalent to the distance between the lateral edges on the other side.

In order to keep the vertebrae in that position relative to one another, numerous alignment devices have been developed for use in spinal fixation. One type of spinal construct may include, for example, one or more spinal rods that can be placed parallel to the spine with fixation devices (such as hooks, screws, or plates) interconnected between the spinal rods at selected portions of the spine.

The process of properly inserting the spinal rod into the receiving slot of one or more bone screws, followed by securing the connecting rod therein, often requires the clinician to use a number of instruments and expend a great deal of time and effort. The repeated process of inserting and securing the spinal rod into one or more bone screws secured to adjacent vertebrae can be difficult, tiresome, and time consuming. Therefore, a continuing need exits for a device that can safely and efficiently reduce the spinal rod into the screw housing and lock the spinal rod in place.

SUMMARY

The present disclosure describes a device for reducing a spinal rod into a screw housing that demonstrates a practical approach to meeting the performance requirements and overcoming usability challenges associated with reducing a spinal rod. In accordance with an embodiment of the present disclosure, there is provided a rod reducer including a shaft, a sleeve assembly defining a first bore dimensioned to receive the shaft therethrough, a housing defining a second bore dimensioned to receive the shaft therethrough, arm members operatively associated with the housing, and an anvil operatively coupled with the shaft. The sleeve assembly includes a locking tab. The housing includes a groove configured to selectively receive the locking tab of the sleeve assembly. The housing includes a locking ledge portion in registration with the groove. The anvil is transitionable between a proximal position, in which, the arm members are spaced apart, and a distal position, in which, the arm members are in an approximated position. The sleeve assembly is rotatable about the shaft between an engaged state in which, the locking tab of the sleeve assembly engages the groove of the housing such that the locking ledge portion inhibits relative axial displacement of the sleeve assembly with the housing, and a disengaged state in which, the locking tab of the sleeve assembly is offset from the groove such that the sleeve assembly is axially movable relative to the housing.

In an embodiment, the sleeve assembly may include a sleeve defining a cavity and a nut disposed in the sleeve. The nut may include the locking tab.

In another embodiment, the locking tab of the nut may extend distally out of the sleeve.

In a further embodiment, the nut may have a cross-section complementary to a cross-section of the cavity of the sleeve for concomitant rotation with the sleeve.

In still another embodiment, the nut may include a pair of transverse wings defining a slot.

In yet another embodiment, the sleeve assembly may further include a biasing member disposed within the slot of the pair of transverse wings. The biasing member may be configured to bias the sleeve proximally.

In yet another embodiment, the nut may include threads configured to threadably engage the shaft.

In still another embodiment, the groove of the housing may include an arcuate profile.

In still another embodiment, the sleeve assembly may be rotated about 90 degrees about the shaft during transition between the engaged and disengaged states.

In still another embodiment, the shaft may be rotatably supported with the anvil such that rotation of the shaft causes axial displacement of the anvil along the arm members.

In still another embodiment, the second bore of the housing may be configured to slidably receive the shaft therethrough.

In still yet another embodiment, the sleeve may include a gripping surface including ridges.

In still yet another embodiment, the anvil may include a saddle including an arcuate profile configured to engage a spinal rod.

In an embodiment, the anvil may define opposing cavities dimensioned to receive the respective arm members therethrough.

In accordance with another embodiment of the present disclosure, there is provided a rod reducer including a shaft, a housing defining a first bore configured to slidably receive the shaft therethrough, a sleeve assembly defining a second bore configured to threadably receive the shaft therethrough, arm members pivotably coupled with the housing, and an anvil operatively coupled with the shaft. The anvil is movable along the arm members, which, in turn, transitions the arm members between an approximated position and a spaced apart position. The sleeve assembly is rotatable about the shaft. The sleeve assembly is transitionable between an engaged state in which the sleeve assembly is engaged with the housing, and a disengaged state in which the sleeve assembly is axially movable relative to the housing.

In an embodiment, the shaft may be non-rotatably slidable through the first bore when the sleeve assembly is in the disengaged state.

BRIEF DESCRIPTION OF THE DRAWINGS

The above and other aspects and features of the present disclosure will become more apparent in light of the following detailed description when taken in conjunction with the accompanying drawings in which:

FIG. 1 is an end view of a rod reducer in accordance with an embodiment of the present disclosure;

FIG. 2 is an end view of the rod reducer of FIG. 1, illustrating the rod reducer partially actuated;

FIG. 3 is a perspective view of the rod reducer of FIG. 2, illustrating the sleeve assembly in a disengaged state;

FIG. 6 is perspective view of a sleeve of the sleeve assembly of the rod reducer of FIG. 1;

FIG. 7 is a top view of the sleeve of FIG. 6;

FIG. 8 is a side view of the sleeve of FIG. 6;

FIG. 9 is an end view of the sleeve of FIG. 6;

FIG. 16 is a perspective view of an arm member of the rod reducer of FIG. 1;

DETAILED DESCRIPTION OF EMBODIMENTS

Figure 4:
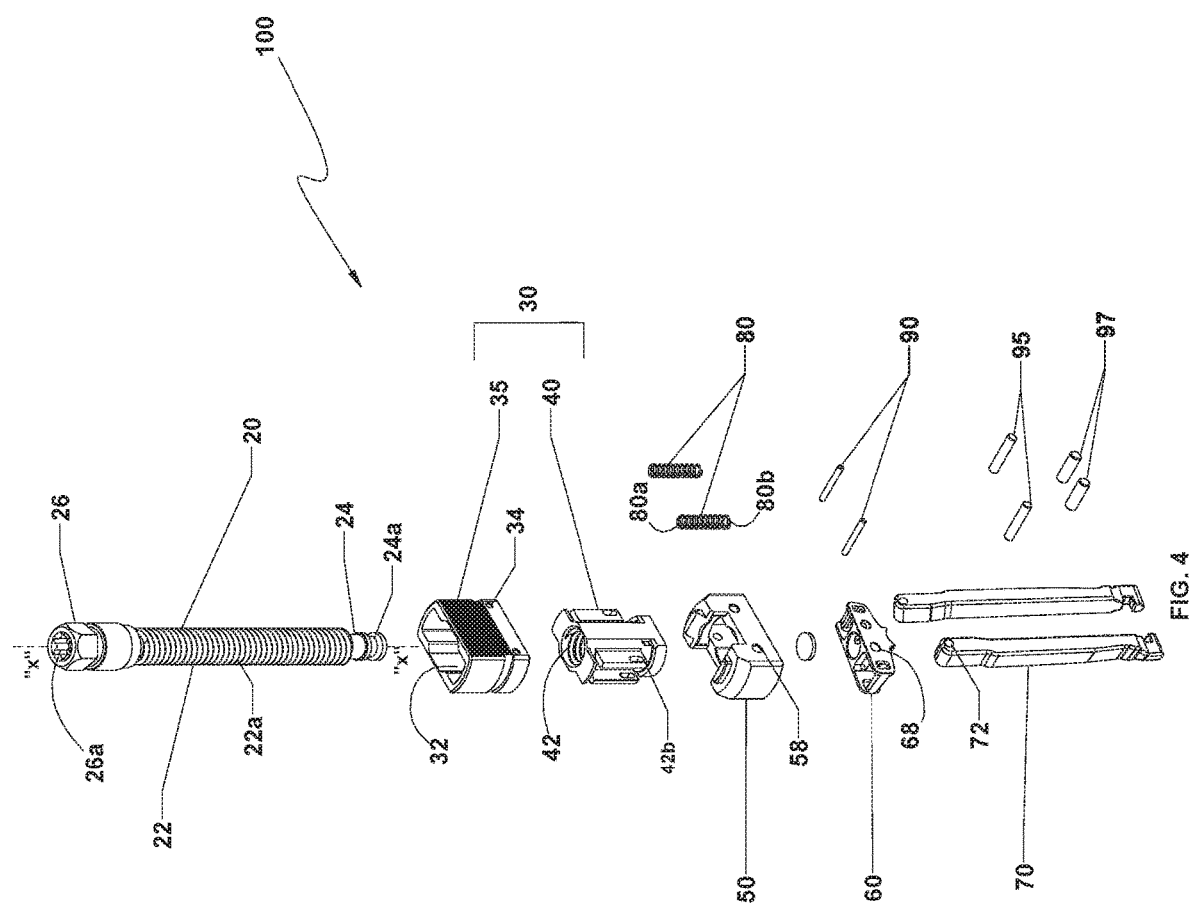
FIG. 4 is an exploded, perspective view of the rod reducer of FIG. 1 with parts separated.
Figure 5:
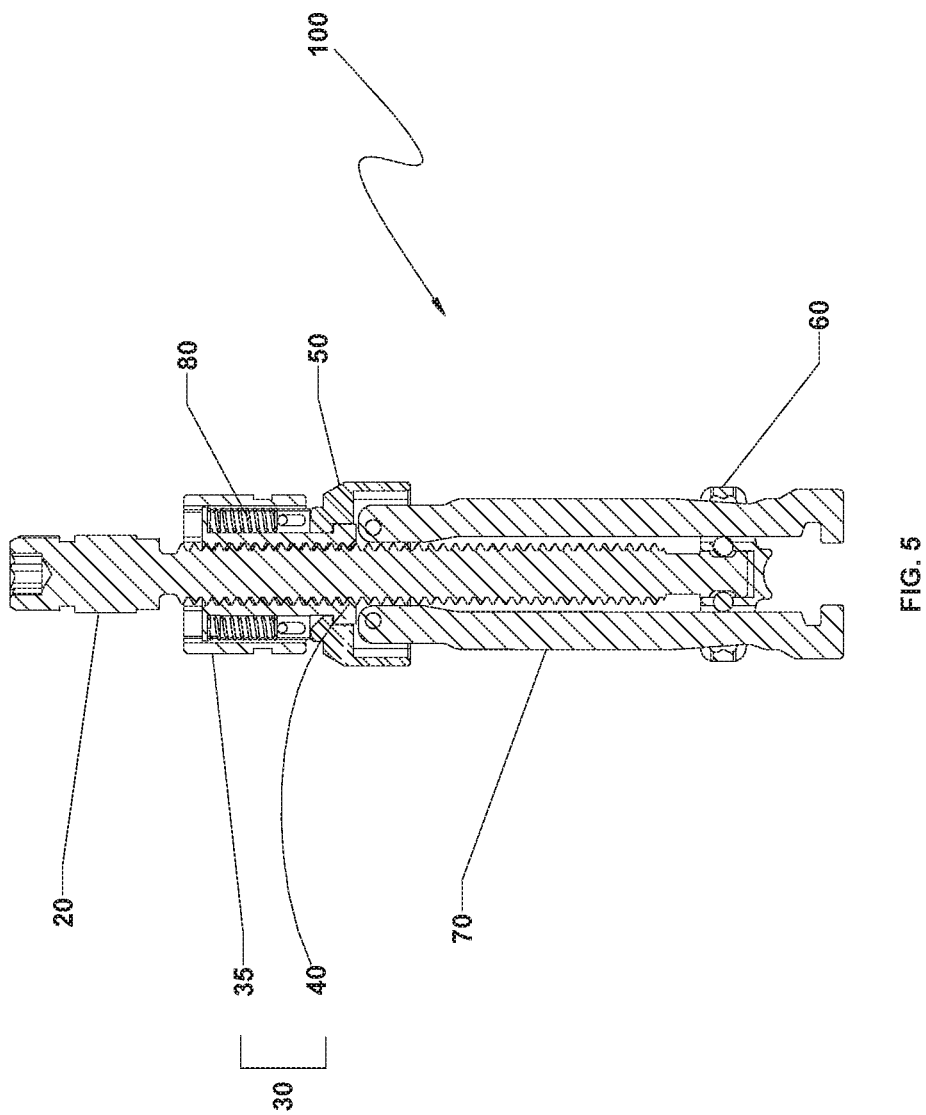
FIG. 5 is a cross-sectional view of the rod reducer of FIG. 1.

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during use. The terms "distal" and "leading" may also be employed interchangeably, and should be understood as referring to the portion of a structure that is farther from the clinician during use. In addition, the term "cephalad" is used in this application to indicate a direction towards a patient's head, whereas the term "caudad" indicates a direction towards the patient's feet. Further still, the term "medial" indicates a direction towards the middle of the body of the patient, while the term "lateral" indicates a direction towards a side of the body of the patient (i.e., away from the middle of the body of the patient). The term "posterior" indicates a direction towards the patient's back, and the term "anterior" indicates a direction towards the patient's front. In the following description, well-known functions or constructions are not described in detail to avoid obscuring the present disclosure in unnecessary detail.

With reference to FIGS. 1-3, a rod reducer in accordance with an embodiment of the present disclosure is generally shown as a rod reducer 100. The rod reducer 100 may be utilized to reduce a spinal rod 200 (FIG. 18) into a slot 332 (FIG. 18) of a screw housing 330 of a bone screw 300. In particular, the rod reducer 100 provides a sleeve assembly 30 that enables quick release or engagement of the rod reducer 100 with the bone screw 300, which, in turn, reduces the time required for surgery and reduces the fatigue experienced by the clinician when compared with manually rotating a shaft 20 in order to disengage or engage the rod reducers 100 with the respective bone screws 300.

With reference to FIGS. 3 and 4, the rod reducer 100 includes a shaft 20, the sleeve assembly 30 including a sleeve 35 and a nut 40, a housing 50, an anvil 60, and arm members 70. The shaft 20 includes an elongate body 22 having threads 22a configured to threadably engage the nut 40, as will be discussed below. The elongate body 22 includes a distal portion 24 defining an annular groove 24a configured to rotatably engage anvil 60, and a proximal portion 26 defining a cavity 26a having, e.g., a hex, key feature for non-slip engagement with a driver or other instrument (not shown) to drive the shaft 20. It is contemplated that cavity 26a may have any suitable configuration such as, e.g., slotted, square, star fitting, or a Phillips head, for engagement with the driver.

With reference to FIGS. 4-9, the sleeve assembly 30 includes a sleeve 35 defining a cavity 32, and a nut 40 configured to be operatively received in the sleeve 35. The sleeve 35 may include opposing gripping surfaces 39 having, e.g., ridges, configured to enhance gripping by the clinician. The sleeve 35 further includes opposing sides 36 extending between the opposing gripping surfaces 39. The opposing sides 36 may have, e.g., an arcuate profile. The opposing sides 36 may define, e.g., respective grooves 38, to further enhance gripping by the clinician or a tool. The sleeve 35 defines bores 34 dimensioned to receive respective pins 90 (FIG. 4) extending through the nut 40, as will be described below.

Figure 12:
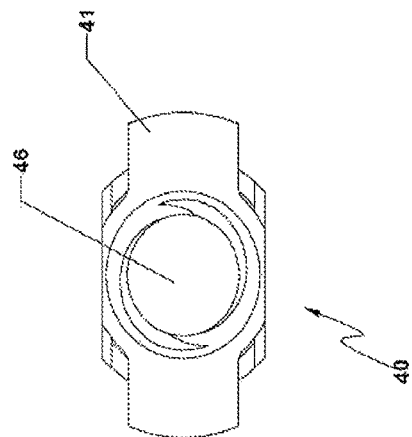
FIG. 12 is a top view of the nut of FIG. 10.
Figure 11:
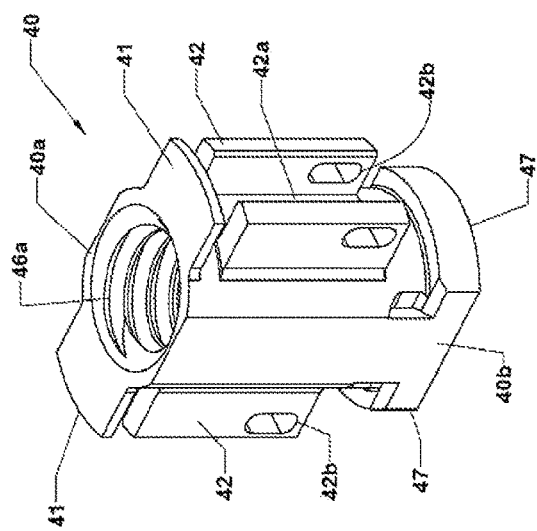
FIG. 11 is a perspective of the nut of FIG. 10.
Figure 10:
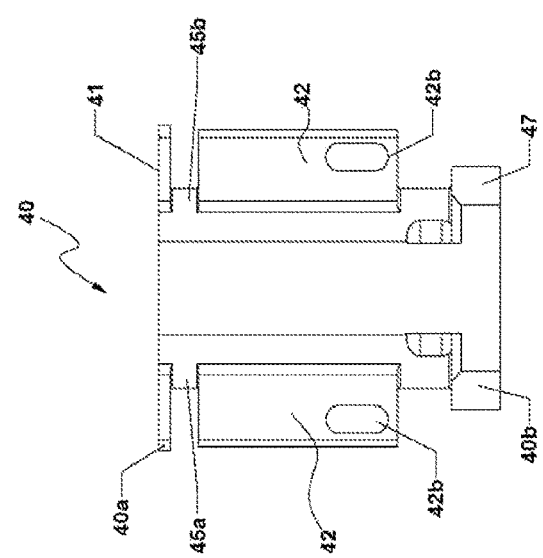
FIG. 10 is an end view of a nut of the sleeve assembly of FIG. 1.

With reference now to FIGS. 10-12, the nut 40 has a shape complementary to a shape of the cavity 32 (FIG. 7) of the sleeve 35 in order to provide concomitant rotation with the sleeve 35, while enabling axial displacement of the nut 40 within the sleeve 35. The nut 40 has a proximal portion 40a and a distal portion 40b. The proximal portion 40a includes opposing anchoring portions 41, and the distal portion 40b includes locking tabs 47 extending distally out of the sleeve 35 when the nut 40 is disposed in the sleeve 35. The nut 40 defines a bore 46 extending between the proximal and distal portions 40a, 40b. Internal walls defining the bore 46 include threads 46a configured to threadably engage the elongate body 22 (FIG. 4) of the shaft 20. In addition, the nut 40 includes a pair of wings 42 on respective lateral sides 45a, 45b of the nut 40. Each pair of wings 42 defines a slot 42a dimensioned to receive a biasing member 80 (FIG. 4) such as, e.g., a spring. The opposing anchoring portions 41 are in communication with the respective slots 42a. In addition, each lateral wing 42 defines a camming slot 42b dimensioned to receive the pin 90 (FIG. 4) therethrough. Under such a configuration, each biasing member 80 (FIG. 4) is received in a respective slot 42a defined by the respective pair of lateral wings 42. A first end 80a of the biasing member 80 is supported against the anchoring portion 41 of the nut 40, and a second end 80b of the biasing member 80 is secured with the pin 90 extending through the camming slots 42b of the lateral wings 42 and the bores 34 (FIG. 4) of sleeve 35. In this manner, the biasing members 80 provide a proximal biasing force on the respective pins 90, which, in turn, provides a proximal biasing force on the sleeve 35.

Figure 15:
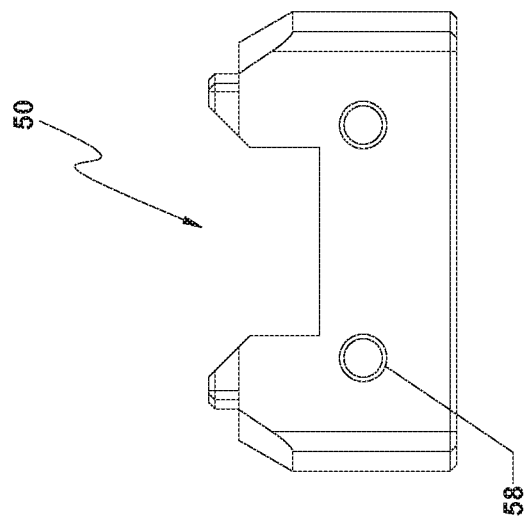
FIG. 15 is a side view of the housing of FIG. 13.
Figure 14:
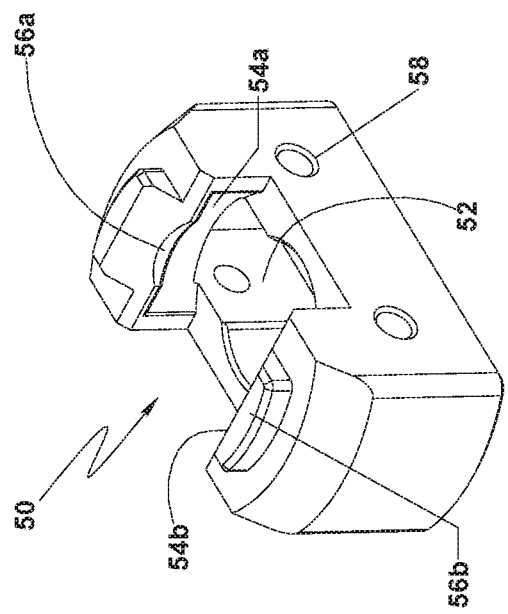
FIG. 14 is a perspective view of the housing of FIG. 13.
Figure 13:
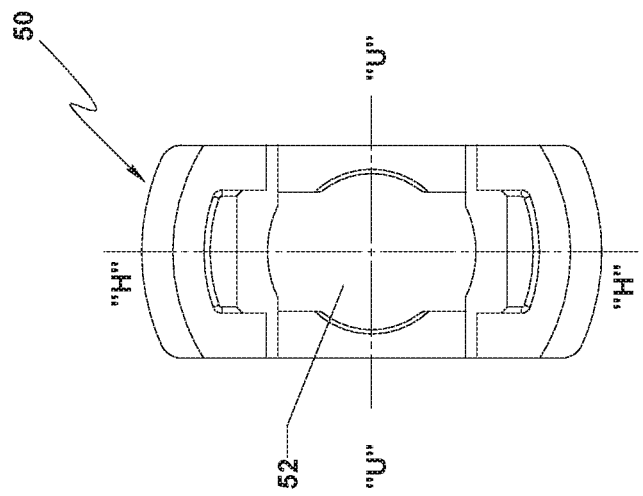
FIG. 13 is a top view of a housing of the rod reducer of FIG. 1.

With reference now to FIGS. 13-15, the housing 50 is coupled with the sleeve assembly 30 and the arm members 70. The sleeve assembly 30 is rotatably coupled with the housing 50 in order to selectively detach the sleeve assembly 30 from the housing 50. The housing 50 defines a bore 52 dimensioned to slidably receive the shaft 20 (FIG. 4) therethrough. The housing 50 defines opposing grooves 54a, 54b about the bore 52. The opposing grooves 54a, 54b are dimensioned to slidably receive the locking tabs 47 (FIG. 11) of the nut 40 of the sleeve assembly 30. Each of the opposing grooves 54a, 54b may include an arcuate profile to facilitate rotation of the locking tabs 47 therethrough. In addition, the housing 50 includes opposing locking ledge portions 56a, 56b in registration with the respective grooves 54a, 54b. Under such a configuration, when the locking tabs 47 of the nut 40 are in registration with the opposing grooves 54a, 54b of the housing 50, e.g., aligned with an axis "L-L" (FIG. 13), the locking ledge portions 56a, 56b inhibit axial displacement of the sleeve assembly 30 relative to the housing 50. However, when the sleeve assembly 30 is rotated such that the locking tabs 47 of the nut 40 are disengaged from the respective grooves 54a, 54b of the housing 50, e.g., the locking tabs 47 of the nut 40 are aligned with an axis "U-U" (FIG. 13) orthogonal to the axis "L-L," the sleeve assembly 30 may be detached or spaced apart from the housing 50 to, e.g., quickly release the arm members 70 (FIG. 16) from the bone screw 300 (FIG. 18), as will be discussed hereinbelow. Under such a configuration, the shaft 20 is non-rotatably slidable through the bore 52 of the housing 50 when the sleeve assembly 30 is disengaged from the housing 50. In this manner, the anvil 60 may be slidably movable along the arm members 70 without having to manually rotate the shaft 20 by the clinician.

With reference now to FIGS. 13-16, the housing 50 is operatively coupled with the arm members 70. In particular, the housing 50 defines pin holes 58 dimensioned to receive respective pins 95 (FIG. 4) extending through bores 72 defined in the respective arm members 70. In this manner, each arm member 70 may be pivotally coupled to the housing 50 such that the arm members 70 are movable between approximated and spaced apart positions. However, it is also envisioned that the arm members 70 and the housing 50 may be integrally formed as a single construct, in which, the arm members 70 are radially deflectable to engage with or disengage from the bone screw 300 (FIG. 18).

With particular reference to FIG. 16, each of the arm members 70 includes an elongate body 70a including a proximal portion 70b and a distal portion 70c. As discussed hereinabove, the proximal portion 70b defines the bore 72 operatively coupled with the housing 50, and the distal portion 70c includes an engaging portion 74 such as, e.g., a hook, configured to engage the bone screw 300 (FIG. 18). In particular, the arm members 70 are secured with the housing 50 such that the arm members 70 diametrically oppose each other in order to enhance securement with the bone screw 300. The elongate body 70a may be formed of a material having low friction to facilitate sliding of the anvil 60 (FIG. 17) therealong.

Figure 17:
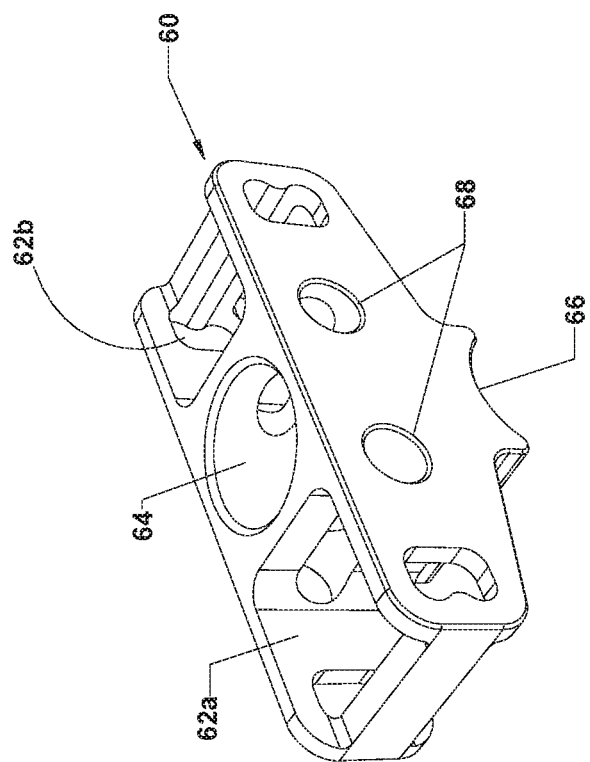
FIG. 17 is a perspective view of an anvil of the rod reducer of FIG. 1.

With reference now to FIG. 17, the anvil 60 defines a bore 64 dimensioned to receive the shaft 20 (FIG. 4), and opposing cavities 62a, 62b about the bore 62. The opposing cavities 62a, 62b are dimensioned to receive the respective arm members 70 (FIG. 16) therethrough. Under such a configuration, axial displacement of the anvil 60 relative to the arm members 70 transitions the engaging portions 74 (FIG. 16) of the arm members 70 between an approximated position, in which, the engaging portions 74 engage the bone screw 300 (FIG. 18), and a spaced apart position, in which, the space created between the engaging portions 74 enables, e.g., disengagement or placement, of the engaging portions 74 with the bone screw 300. In addition, the anvil 60 further defines pin holes 68 dimensioned to receive respective pins 97 (FIG. 4) configured to be received in the annular groove 24a (FIG. 4) defined in the distal portion 24 of the shaft 20 (FIG. 4). The pins 97 diametrically oppose each other. Under such a configuration, the pins 97 disposed in the annular groove 24a of the shaft 20 enable rotation of the shaft 20, while inhibiting axial displacement of the shaft 20 relative to the anvil 60.

Figure 18:
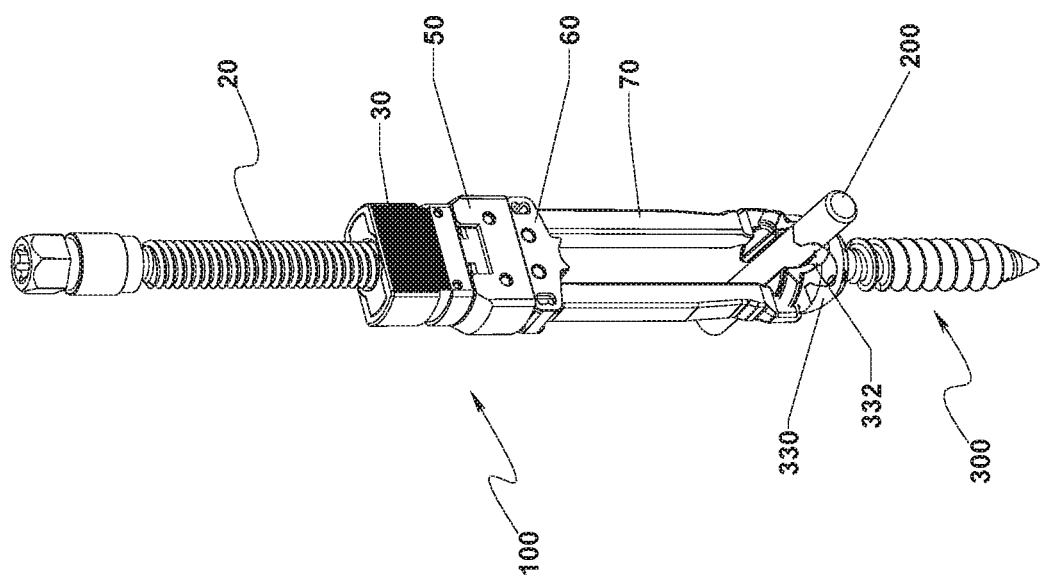

The anvil 60 further includes a saddle 66 configured to reduce the spinal rod 200 (FIG. 18) into a slot 332 defined in a screw housing 330 of the bone screw 300 (FIG. 18). The saddle 66 may include an arcuate or convex profile to facilitate reduction of the spinal rod 200. The saddle 66 may be configured to accommodate a range of spinal rod diameters. For example, the saddle 66 may be adapted to cooperatively engage with a spinal rod 120 having a diameter ranging from about 3 mm to about 8 mm, while still providing the driving force necessary to secure the spinal rod 200 into the bone screw 300.

Figure 19:
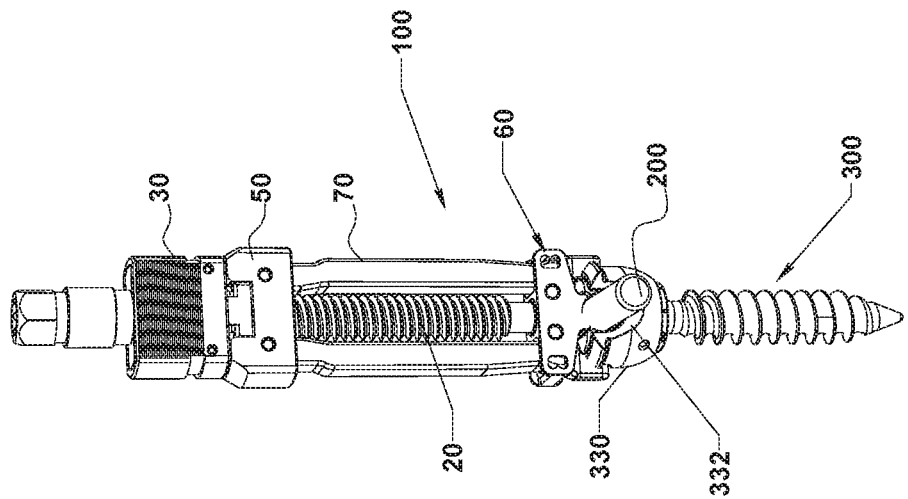
FIGS. 18 and 19 are perspective views of the rod reducer of FIG. 1, illustrating use with a spinal rod and a bone screw.

In use, with reference to FIGS. 18 and 19, the clinician initially prepares the vertebrae (not shown). The bone screws 300 (FIG. 18) are positioned at desired locations on the spine in order to provide the desired placement and securement of the spinal rods 200. Once the desired number of the bone screws 300 have been implanted, the clinician aligns and manipulates the spinal rod 200 such that a portion of the spinal rod 200 is in proximal relation to the screw housings 330 of the respective bone screws 300. Prior to using the spinal rod 200, the clinician may manipulate the spine to a desired curvature. In addition, the spinal rod 200 may be bent using a bending tool (not shown) as known in the art, to the configuration of the desired spinal curvature such as, e.g., the sagittal curve. Thereafter, the clinician may position the pre-bent spinal rod 200 relative to the bone screws 300.

Next, the clinician positions the rod reducer 100 into proximity with the respective bone screw 300, such that the engaging portions 74 of the arm members 70 of rod reducer 100 is in near abutment to the screw housing 330 of the bone screws 300. Next, the clinician causes the engaging portion 74 of the arm members 70 to grasp or otherwise affix to the screw housing 330 by rotating the shaft 20. Manually rotating shaft 20 such a distance can be cumbersome, tedious, and time consuming. Thus, while the sleeve assembly 30 may be utilized for the quick release feature, the clinician may also slide the shaft 20 distally through the housing 50 to cause the engaging portions 74 to engage the screw housing 330, while the sleeve assembly 30 is disengaged from the housing 50. The shaft 20 may be threaded into the sleeve assembly 30 by a pre-determined amount prior to the surgical procedure.

The rod reducer 100 provides a mechanical advantage to further bend or shape the spinal rod 200, while the spinal rod 200 is securely held by the rod reducer 100 and the screw housing 330 of the bone screw 300. In this configuration, the clinician may make final adjustments to the spinal rod 200. After spinal rod 200 is properly aligned, the clinician may further reduce spinal rod 200 to secure the spinal rod 200 into the screw housing 330 of the bone screw 300. Thereafter, the clinician reduces the spinal rod 200 into the slot 332 of the screw housing 330. For example, there may be about 15 mm or more of travel required in order to reduce the spinal rod 200 fully within the saddle 332 of the screw housing 330 such that spinal rod 200 and screw housing can be locked.

With a plurality of rod reducers 100 mounted to different bone screws 300, the clinician is able to gradually reduce the spinal rod 200 to a plurality of bone screws 300 by sequentially reducing each rod reducer 100 fully or partially until all of the rod reducers 100 have been actuated fully and the spinal rod 200 is reduced into all of the bone screws 300.

Upon final alignment of spinal rod 200 between the bone screws 300, and/or securement of spinal rod 200 into the screw housing 330 thereof, the clinician may decouple the rod reducers 100 from the respective bone screws 300 by rotating the respective sleeve assemblies 30 such that the locking tabs 47 of the nut 40 are offset from the locking ledge portions 56a, 56b of the housing 50. At this time, the shaft 20 may be pulled proximally, which, in turn, transitions the arm members 70 to be spaced apart and enables the clinician to disengage the rod reducer 100 from the bone screw 300. Alternatively, the shaft 20 may be manually rotated in order to move the shaft 20 proximally. As the clinician translates anvil 60 towards the proximal position, the arm members 70 of the respective rod reducer 100 may be decoupled from the bone screw 300, permitting the clinician to detach the rod reducer 100 from the respective bone screw 300.

It is contemplated that the rod reducer 100 may be provided in a kit that includes the rod reducer 100, the bone screws 300, the spinal rods 200, and an orthopedic tool (not shown) including, e.g., a tightening or loosening tool, an alignment tube, or a locking device.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus, the scope of the embodiments should be determined by the claims of the present application and their legal equivalents, rather than by the examples given.

What is claimed is:

1. A rod reducer comprising:
    a shaft;
    a sleeve assembly defining a first bore dimensioned to receive the shaft therethrough, the sleeve assembly including a locking tab;
    a housing defining a second bore dimensioned to receive the shaft therethrough, the housing including a groove configured to selectively receive the locking tab of the sleeve assembly, the housing including a locking ledge portion in registration with the groove;
    arm members operatively associated with the housing; and
    an anvil operatively coupled with the shaft, the anvil transitionable between a proximal position, in which, the arm members are spaced apart, and a distal position, in which, the arm members are in an approximated position,
    wherein the sleeve assembly is rotatable about the shaft between an engaged state in which, the locking tab of the sleeve assembly engages the groove of the housing such that the locking ledge portion inhibits relative axial displacement of the sleeve assembly with the housing, and a disengaged state in which, the locking tab of the sleeve assembly is offset from the groove such that the sleeve assembly is axially movable relative to the housing.

2. The rod reducer according to claim 1, wherein the sleeve assembly includes a sleeve defining a cavity and a nut disposed in the sleeve, the nut including the locking tab.

3. The rod reducer according to claim 2, wherein the locking tab of the nut extends distally out of the sleeve.

4. The rod reducer according to claim 2, wherein the nut has a cross-section complementary to a cross-section of the cavity of the sleeve for concomitant rotation with the sleeve.

5. The rod reducer according to claim 2, wherein the nut includes threads configured to threadably engage the shaft.

6. The rod reducer according to claim 2, wherein the nut includes a pair of transverse wings defining a slot.

7. The rod reducer according to claim 6, wherein the sleeve assembly further includes a biasing member disposed within the slot of the pair of transverse wings, the biasing member configured to bias the sleeve proximally.

8. The rod reducer according to claim 1, wherein the groove of the housing includes an arcuate profile.

9. The rod reducer according to claim 1, wherein the sleeve assembly is rotated about 90 degrees about the shaft during transition between the engaged and disengaged states.

10. The rod reducer according to claim 1, wherein the shaft is rotatably supported with the anvil such that rotation of the shaft causes axial displacement of the anvil along the arm members.

11. The rod reducer according to claim 1, wherein the second bore of the housing is configured to slidably receive the shaft therethrough.

12. The rod reducer according to claim 1, wherein the sleeve includes a gripping surface including ridges.

13. The rod reducer according to claim 1, wherein the anvil includes a saddle including an arcuate profile configured to engage a spinal rod.

14. The rod reducer according to claim 1, wherein the anvil defines opposing cavities dimensioned to receive the respective arm members therethrough.

15. A rod reducer having a longitudinal axis comprising:
    a shaft;
    a housing defining a first bore configured to slidably receive the shaft therethrough;
    a sleeve assembly defining a second bore configured to threadably receive the shaft therethrough, when the shaft extends through the first bore and the second bore;
    1) the sleeve assembly is rotatable relative to the housing, about the shaft, and
    2) the sleeve assembly is transitionable between an engaged state in which the sleeve assembly is engaged with the housing, and a disengaged state in which the sleeve assembly is axially movable along the longitudinal axis of the rod reducer relative to the housing;
    arm members pivotably coupled with the housing; and
    an anvil operatively coupled with the shaft, the anvil movable along the arm members, which, in turn, transitions the arm members between an approximated position and a spaced apart position.

16. The rod reducer according to claim 15, wherein the shaft is non-rotatably slidable through the first bore when the sleeve assembly is in the disengaged state.

17. The rod reducer according to claim 15, wherein the housing defines a groove and the sleeve assembly includes a locking tab configure to be selectively received in the groove, the housing including a locking ledge portion in registration with the groove, wherein when the locking tab of the sleeve assembly engages the groove, the locking ledge portion inhibits axial displacement of the sleeve assembly with respect to the housing.

18. The rod reducer according to claim 17, wherein the sleeve assembly includes a sleeve and a nut disposed within the sleeve for concomitant rotation with the sleeve, the nut is configured for axial translation relative to the sleeve, the sleeve having the locking tab extending distally out of the sleeve.

19. The rod reducer according to claim 17, wherein the groove of the housing has an arcuate profile.

20. The rod reducer according to claim 18, wherein the sleeve assembly includes a biasing member to bias the sleeve proximally.

* * * * *